United States Patent
Briant (10) Patent No.: US 11,291,575 B2
(45) Date of Patent: Apr. 5, 2022

(54) HEADREST DEVICE WITH ELASTIC MEANS FOR RETURN TO A NOMINAL POSITION

(71) Applicant: Paul Briant, Trémouille (FR)

(72) Inventor: Paul Briant, Trémouille (FR)

(*) Notice: Subject to any disclaimer, the term of this patent is extended or adjusted under 35 U.S.C. 154(b) by 0 days.

(21) Appl. No.: 16/336,078

(22) PCT Filed: Oct. 18, 2017

(86) PCT No.: PCT/FR2017/052870
§ 371 (c)(1),
(2) Date: Mar. 22, 2019

(87) PCT Pub. No.: WO2018/073540
PCT Pub. Date: Apr. 26, 2018

(65) Prior Publication Data
US 2019/0290468 A1    Sep. 26, 2019

(30) Foreign Application Priority Data
Oct. 18, 2016  (FR) ...................................... 1601511

(51) Int. Cl.
*A61F 5/058*     (2006.01)
*A41D 13/05*     (2006.01)
*A61F 5/01*      (2006.01)

(52) U.S. Cl.
CPC ...... *A61F 5/05883* (2013.01); *A41D 13/0512* (2013.01); *A61F 5/01* (2013.01); *A41D 2300/33* (2013.01)

(58) Field of Classification Search
CPC ........ A61F 5/05883; A61F 5/01; A61F 5/055; A41D 13/0512; A41D 2300/33; Y10S 128/23; A42B 3/0473; A47C 7/383
See application file for complete search history.

(56) References Cited

U.S. PATENT DOCUMENTS 2,820,455 A * 1/1958 Hall .................. A61F 5/055
                                                    602/18
3,105,489 A * 10/1963 Zivi .................. A61H 1/0229
                                                    602/32
(Continued)

FOREIGN PATENT DOCUMENTS

| CN | 201847198 U | 6/2011 |
| EP | 0336074 A2 | 10/1989 |
| FR | 3019973 A1 | 10/2015 |

OTHER PUBLICATIONS

International Search Report for PCT/FR2017/052870, dated Dec. 6, 2017.

(Continued)

*Primary Examiner* — Khoa D Huynh
*Assistant Examiner* — Erick I Lopez
(74) *Attorney, Agent, or Firm* — Merchant & Gould P.C.

(57) ABSTRACT

A headrest device includes a headrest (1) which is movably mounted on a back support (3) associated with a harness (4) for holding the back support on the back of a user. The headrest is mounted to elastically slide in longitudinal translation along the back support and is elastically attached to the back support in an articulated manner to tilt transversely. The headrest is used continuously according to the movements of the head in extension thereof towards a nominal resting position. The device may include a first torsion spring acting antagonistically in relation to the transverse tilting movements of the headrest and a compression spring acting antagonistically in relation to the longitudinal translation movements of the headrest. The two springs act synchronously during operation, continuously tracking movements of the head of the wearer in relation to a nominal rest position, with non-sliding support at the back of the head.

28 Claims, 3 Drawing Sheets

(56) References Cited

U.S. PATENT DOCUMENTS

| | | | | |
|---|---|---|---|---|
| 3,548,817 | A | * | 12/1970 | Mittasch ................. A61F 5/024 602/36 |
| 3,776,224 | A | * | 12/1973 | McFarland ............. A61F 5/055 602/18 |
| 5,466,214 | A | * | 11/1995 | Calderon-Garciduenas ................ A61F 5/026 602/19 |
| 6,308,345 | B1 | * | 10/2001 | Williams, Jr. ..... A41D 13/0512 2/467 |
| 7,892,193 | B2 | * | 2/2011 | Marchetto ............... A61F 5/055 602/18 |
| 2008/0228121 | A1 | | 9/2008 | Hughes |
| 2010/0204628 | A1 | * | 8/2010 | Ghajar ................... A61F 5/055 602/18 |

OTHER PUBLICATIONS

Kapandji as reported on p. 18 in Biomechanics of Cervical Spine, Instability Concept Symposium, Cervical Spine, Barcelona, Feb. 2014. One page.

Chinese Office Action for Chinese Patent Application No. 201780059032.0 dated Feb. 1, 2021 (4 pages).

* cited by examiner

HEADREST DEVICE WITH ELASTIC MEANS FOR RETURN TO A NOMINAL POSITION

This application is a National Stage Application of PCT/FR2017/052870, filed Oct. 18, 2017, which claims benefit of French Patent Application No. 1601511, filed Oct. 18, 2016, and which applications are incorporated herein by reference. To the extent appropriate, a claim of priority is made to each of the above-disclosed applications.

The invention relates to a headrest device of the type mainly designed to improve the comfort of users who must hold their head in extension, i.e. tilted rearwards, for a long period of time and/or in a frequently repeated manner.

In situations where an individual must maintain the head tilted rearwards for a long time, for several hours sometimes, or when they are led to frequently look upwards, this is followed by pain, even lesions, at the level of the neck and vertebrae. As such, the movements of the head in extension rearwards are particularly uncomfortable and with far-reaching consequences because of the compression created on the rear of the cervical vertebrae.

Such situations can be encountered for example in the field of climbing for the assurance of a climber carried out by a person who must maintain constant visual contact from the ground on the climber in order to ensure their safety as much as possible. These types of situations are encountered particularly with workers in many fields, for example for construction employees, when in particular they have to apply coatings or paint at a height, on the ceiling in particular, or for technicians that work on aerial lines of electrical or telephone circuits, or for mechanics that work under vehicles. Experience shows that working in a reclined position on the back is particularly hard, and that it is particularly difficult to ensure a satisfactory comfort for people working under these conditions.

Headrest devices have already been proposed comprising elastic connection means between a fixed back support that is arranged on the back of the wearer and a supporting headrest on the base of the head of the wearer, therefore on the occipital bone. Mention will be made more particularly of patent document FR 3 019 973, of which the content is incorporated herein, in particular in that it describes a mounting with an elastic tilting of the headrest on the back support. The same document proposes a mode of axial mounting of the headrest on the back support which is adjustable, but rigid.

With the aim of providing even more comfort to the user and to adapt to more severe conditions, by avoiding fatigue and musculoskeletal disorders, with the concern also for improving the manufacturing conditions of the device as a whole and in providing more flexibility in the adaptation thereof to each particular wearer, the present invention proposes, in the main, to equip the headrest device with means of elastic extension of the back support axially applying the headrest to a nominal resting position against movements of the head of the wearer tending to sink it into the back support.

Using the elastic means for return of the headrest to the nominal position thereof with respect to the back support which act simultaneously antagonistically with the tipping movements of the headrest in the hinged mounting thereof on the back support and antagonistically with the longitudinal translation movements of the headrest tending to shorten the back support, the invention makes it possible for a constant monitoring of the movements of the head of the wearer in extension with non-sliding support at the level of the back of the head (the occipital bone of the cranium). The quality of the monitoring without sliding that can thus be obtained when the headrest is mounted both elastically sliding in longitudinal translation along the back support and elastically hinged on the back support in transversal tipping, gives the device according to the invention a comfort that cannot be obtained by devices of which the elastic return means had action only on the tipping movement of the headrest in correspondence with the variations in tilting of the head rearwards in the extension movements thereof. Yet, in practice, it can be observed that the head in extension tends to sink from top to bottom at the same time as it is inclines from front to the rear.

In the preferred embodiments of the invention, means for adjusting said elastic return means are furthermore provided, making it possible to define the nominal position of the headrest with respect to the back support in correspondence with an initial resting position deemed as natural for the head of the user. Such adjustment means are advantageously accessible to the user, including when they are wearing the headrest device and, where applicable, during their work on a construction site. They are advantageously designed to act as an adjustment of the initial tilting of the headrest on the back support (in correspondence with a carrying of the head in natural extension) as well as in an adjustment of the longitudinal position of the mounting hinged on the back support (in correspondence with a neck height deemed as the most comfortable by the user), therefore as an adjustment of an initial extension of the back support.

It is thus, in particular, that the elastic return means of the headrest with respect to the back support can at best comprise, on the one hand, a torsion spring bearing on the headrest (in particular a part of this one forming a stiffener when it is surrounded with flexible material for questions of contact comfort) and on an upper bearing surface of a slider slidably mounted in the main body of the back support, and on the other hand, a compression spring maintained in a guide bore inside the slider and that tends to deploy this by extending the back support.

Advantageously, the device according to the invention, has means for adjusting the dimensional characteristics thereof that make it possible to adjust it to the morphology of the user and/or to the desired comfort, particularly with regards to their neck height and their cervical flexibility. In particular, it is possible notably to provide for this purpose, means for adjusting the initial position of the slider as longitudinally exceeding with respect to the back support when the compression of the spring between them is assumed to be zero, at least marginal for the user who is holding their head naturally, in the resting position.

The headrest device according to the invention can advantageously be equipped with various adjustment means that make it possible for a finer adjustment of the conditions concerning the use thereof, with the aim of adapting it on a case-by-case basis, on the one hand, to the user wearing the device, on the other hand, to each situation of use, by improving, each time, the feeling of the user. It is thus, that it is possible to provide, in particular, means for adjusting the return effects provided by each one of the two springs, which means will preferably be accessible to the wearer while using the device, without there being a need for them to remove this or to change position. From this point of view, it is particularly advantageous to provide means for adjusting the stiffness of the compression spring which forms the means of elastic extension of the back support.

Preferably, according to the invention, the headrest device comprises, in addition to the mechanical portion, a harness portion formed by a harness made of straps attached to one another at various attaching points which are preferably adjustable, some at the start according to the specific morphology of the person who will use the device, and the others by the user themselves according to the comfort that they are seeking in each position and each specific application. The adjustments to be made by the user when they are already wearing the device on themselves can advantageously be done by acting on the length of the straps.

The role of this harness is to maintain the back support of the mechanical portion firmly in place on the top of the torso in the back of the user wearing same and to equally balance the forces to be supported from this mechanical portion, in particular by bringing them partially to the chest of the wearer so as to relieve their back. A harness with straps that is particularly effective in relieving the lumbar vertebrae, and particularly in relieving cervical vertebrae in situations where the head of the wearer is placed in extension, consequently with an effect of preventing arthrosis, comprises straps extending from shoulders to thigh straps that cross over the chest.

The invention will now be described more completely in the scope of preferred characteristics and the advantages thereof, by making reference to specific embodiments of the headrest device according to the invention, shown by FIGS. 1 to 6, wherein.

Figure 4:
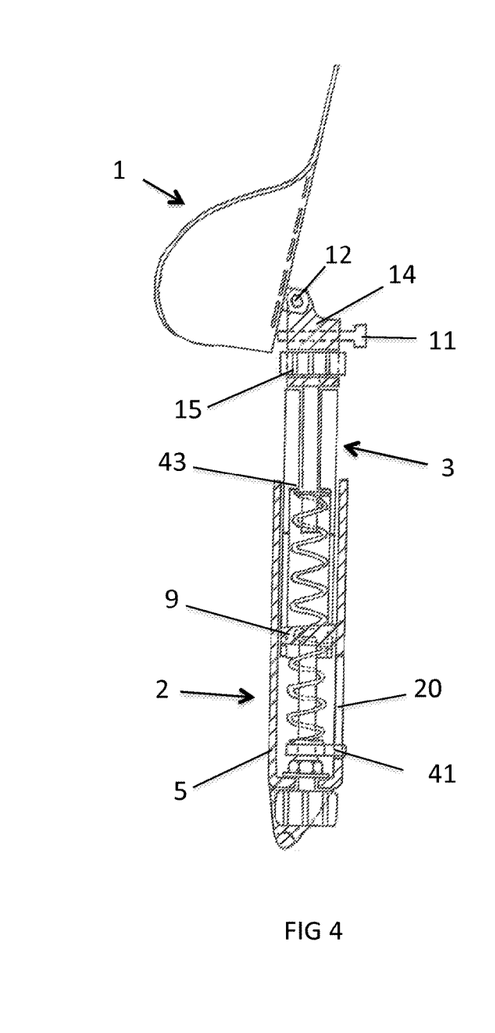
FIG. 4 shows the same device as a profile view.
Figure 5:
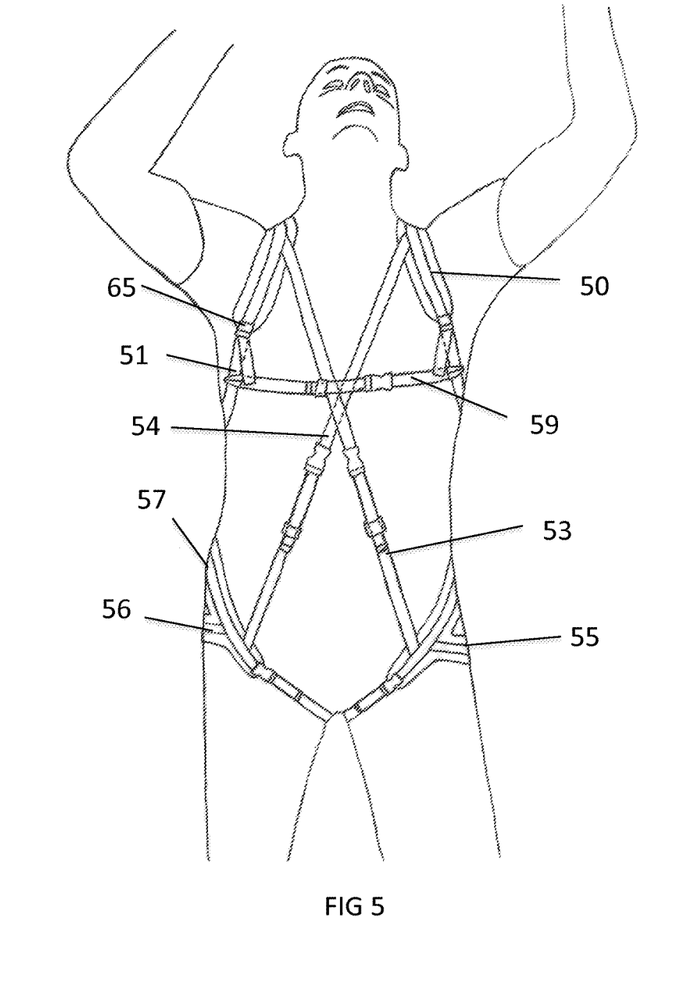
FIG. 5 shows how the harness portion of the headrest device according to the invention is formed, which here is shown when the harness is attached on a user wearing same, in a view towards the front face of the torso of the user.
Figure 6:
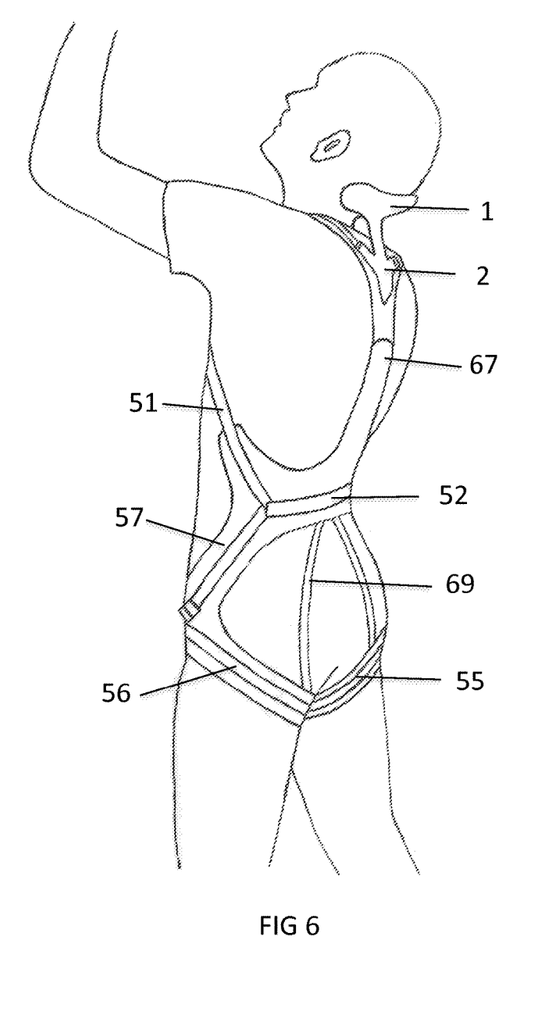
FIG. 6 schematically shows the user wearing the headrest device in a profile view.

According to the invention, the headrest device described here, such as it is shown in the figures, mainly comprises a mechanical portion and a harness portion, carried out with straps that are attached to one another. The elements of the mechanical portion (FIGS. 1 and 3-4) mainly comprise a headrest 1 which is mounted hinged in tipping at the end of a slider 3 which itself is slidably mounted longitudinally with respect to a support element of the mechanical unit which forms what is referred to here as a back support 2, with the reasons that it is worn fixed at the top of the back of the user wearing the headrest device, as can be seen in FIGS. 5 and 6. According to the invention, the hinged mounting, as well as the sliding mounting are associated with elastic return means that apply the headrest to a nominal position that corresponds to a natural carrying of the head of the user at rest.

In the present description, the directions and orientations are defined in reference to the user standing up, with the vertical being along their vertebral column, and front and rear corresponding to the ventral side and to the dorsal side of the wearer respectively.

The headrest 1 is configured to mould the curved shape whereon the rear of the head of a user is bearing in particular when the head is tilted rearwards. More specifically, the headrest is mainly formed by a main part, or internal plate 10, that receives the head of the wearer; it is on this that the occipital base of the cranium rests against. This part is rigid, but advantageously covered with a casing made of flexible material, such as an organic polymer foam, for questions of contact comfort. It is preferably made from a material with shape memory, such that it can be given a curved shape adapted on a case-by-case basis to mould as best as possible the occipital shape of the person to whom is intended each specific headrest device.

Figures 1, 2:
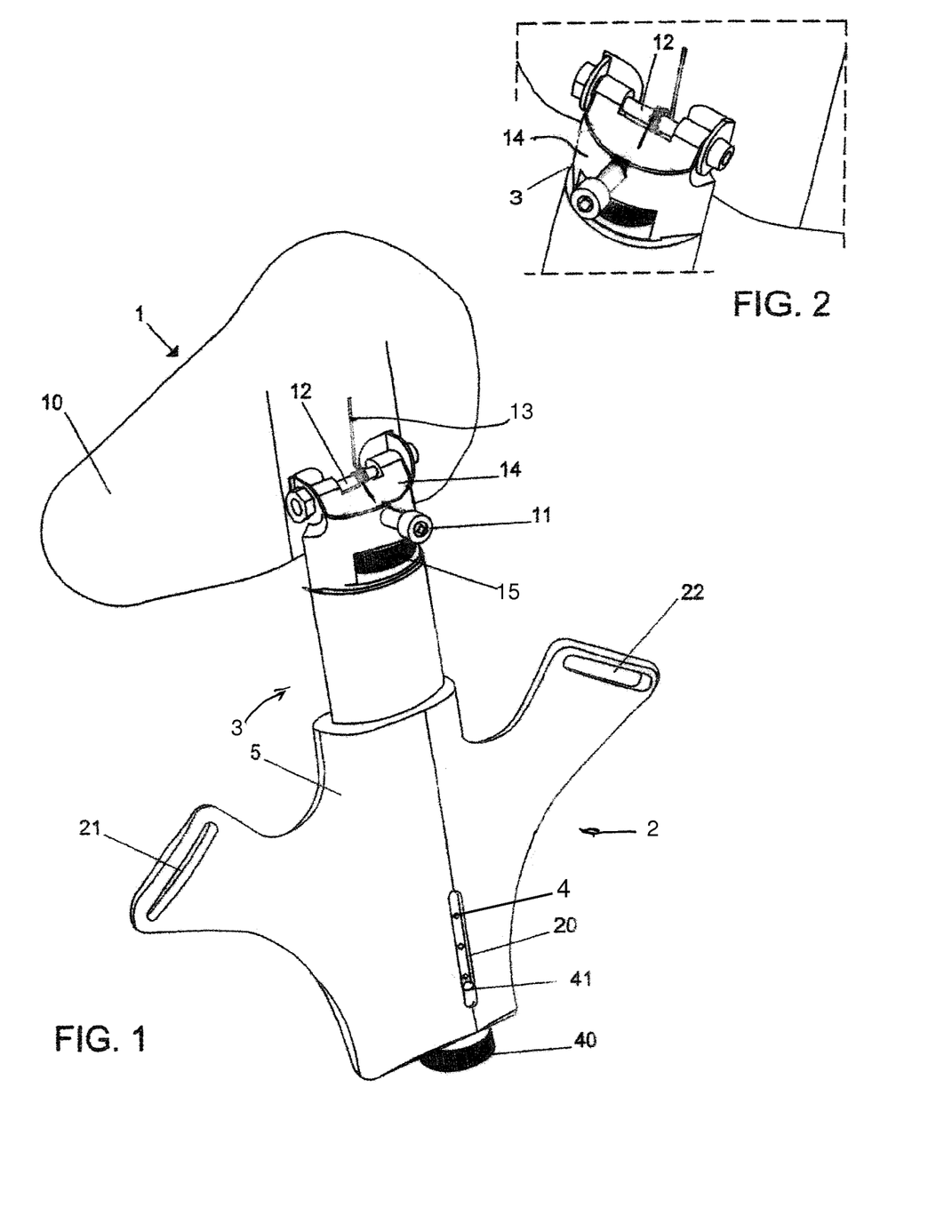
FIG. 1 is a perspective view that shows a headrest device according to the invention described in the mechanical elements thereof, without the harness with straps.
FIG. 2 shows a detail of FIG. 1, in a view from another angle, of the top end of the mechanical portion.

The headrest 1 is mobile in tipping from the front to the rear by rotation at the level of the internal plate 10 thereof about an axis of transversal articulation materialised by a rod 12 of which the ends are retained through ear pieces protruding from the part 10 which are situated fixed in prominence on the rear of the headrest in the bottom portion of this. This rod is an axis of the hinge on an end-piece 14 with hipped sides that terminates the slider 3, as shown in FIGS. 1 and 2.

The movements of the headrest 1 in rotation about the axis of articulation, or hinge axis, are exerted against a torsion spring 13 wound around the rod 12 that bears against by one of the end tabs thereof on the rear of the plate 10 inside the headrest and of which the other end tab is situated bearing on the end-piece 14. The direction of winding of the spires of the spring on the axis rod 12 is defined so as to obtain the torsion of the spring when the headrest is tilted rearwards, which is thus applied to return frontwards into the initial nominal position thereof.

An adjustment screw 11 makes it possible to fix the initial tilting of the headrest. This screw passes through the slider 3 in the central portion thereof until a suitable abutment fixedly formed on the rear of the headrest, and more specifically here until abutting against the internal plate 10, on the rear face thereof. It has a knurled head, which makes it possible for the user already wearing the device to handle it in order to adjust the force of the spring in operation.

The back support 2 forms a main body 5, which is placed vertically running along the vertebral column of the wearer in operation, and two symmetrical wings ended by slots 21 and 22 used to attach the shoulder straps of the harness. The body 5 is hollow in the upper portion thereof, in order to slidingly receive the slider 3. It contains a compression spring, of which the spires in 4 in FIG. 1 appear.

This spring forms part, as does the torsion spring 13, of the elastic return means that return the headrest to the nominal position thereof against the forces exerted by the wearer of the device during their head movements in extension. The two springs act simultaneously, one on the extension of the back support that fixes the position in height of the neck of the hinged connection of the headrest on the back support, the other on the tilting thereof about the axis of articulation.

More specifically, the compression spring 4 is contained guided between opposite bearing surfaces provided, one on the slider 3, the other in the back support 2 in the lower portion thereof, to form abutments between which the spring is more or less compressed when the distance between the two abutments varies. Although this is not shown in detail in the figure, it can be understood, by way of example, that the slider 3 has a longitudinal bore wherein the spring penetrates upwards until a bottom whereon it abuts at the upper end thereof and that the movements of the slider 3 in the back support 2 can advantageously be guided by sliding of lugs in cooperating longitudinal through holes.

The initial position of the slider 3 in the back support 2 can be adjusted by means of a screw, screwed into the material of the slider, which is used to sink it in more or less, by thus modifying the position of the top abutment of the spring 4. This screw can be handled by the user, by means of a knurled head 15 which itself can be accessed through a window arranged in the slider (FIG. 1). This is how the position that takes the articulation hinge of the headrest in the so-called nominal position thereof can be adjusted. An initial position can be adjusted to adapt the headrest device to the length of the neck of the usual user thereof and more fine adjustments can be controlled by the user while they are wearing the device.

The effects of the compression spring are moreover, themselves adjustable. To this effect, the device described here as an example comprises means for moving the abutment on which the spring bears at the bottom end thereof, opposite the end thereof abutting on the slider. It is thus, that FIG. 1 shows the knurled head 40 of a worm screw inside the body 5 of the back support that meshes with a nut integrated with the bearing surface as a bottom abutment for the compression spring. This nut (or an equivalent tapped hole) is maintained immobilised in rotation. Indeed, it has a lug 41 that remains guided in a vertical slot 20 of the body of the back support. By acting on the screw head 40, accessible at any time at the bottom of the headrest, the initial rate of compression of the spring is adjusted. The lug 41 being visible in the slot 20, it provides visual information relating to the stiffness of the compression spring 4.

Figure 3:
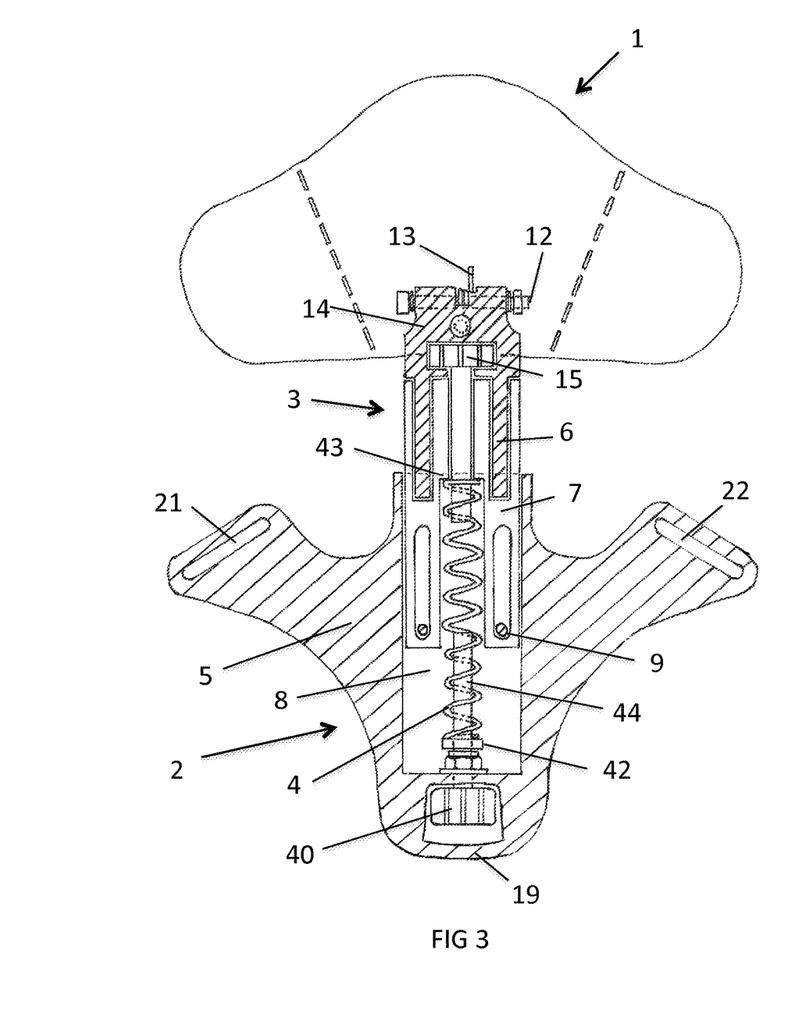
FIG. 3 shows an alternative embodiment of the mechanical portion of the device in a longitudinal cross-sectional view.

In reference now to FIGS. 3 and 4, an alternative embodiment of the device of the invention will be described in more detail wherein the slider 3 is carried out telescopically in combination with means for adjusting the stiffness of the compression spring that applies the headrest in movement along the back support in a deformation of elastic extension of the back support.

In this embodiment, there are the same main elements as in the preceding embodiment, of which the headrest 1, the back support 2 and the slider 3. Producing the latter complies with the headrest being elastically mounted tipping in rotation about a pivot axis 12 transversal to the longitudinal direction of the back support 2 thanks to the torsion spring 13. It will be noted here, that as an alternative, a similar mounting with elastic tipping of the headrest could be materialised in the form of a flexible plate as has been described in the prior patent mentioned hereinabove while still remaining in the scope of the invention. Nevertheless the mounting with tipping about a hinge rod as described in reference to the figures is preferred for the ease of adjustment that it offers.

The slider 3 is composed of an upper element 6, ended by the end-piece 14 whereon bears the spring 13, and a lower element 7, that slides inside the body 5 of the back support. The upper element has an annular section so as to longitudinally slide in a receiving cavity arranged in the material of the lower element 7. More precisely, the section is semi-annular as the face of the back support which is placed against the back of the user is flat.

The initial tilting of the headrest is as hereinabove adjustable by means of the knurled head screw 11 of which the tip is supported on a rigid median portion of the headrest and which is screwed into the material of the end-piece 14 ending the upper element 6 of the slider 3.

Inside the body 5 of the back support, there is also a compression spring 4 of which the action is exerted between two opposite abutments inside a bore 8 arranged to receive it in the body 5 of the back support and in the slider 3, more precisely here in the lower element 6 of the slider. The bearing surface inside the slider 3 (considered as a whole of the two elements that it is formed of) which formed bearing abutment of the compression spring 4 at the upper end thereof is located in 43 at the bottom of said bore. This top abutment for the compression spring is adjustable in the axial position thereof by controlling a relative movement of sliding between the two elements of the slider. This adjustment of the longitudinal position of the top abutment 43 within the slider 3 is ensured, manually from the outside of the unit, by a screw that is screwed into the material of the lower element 7 of the telescopic slider and of which the knurled head 15 is housed in an open cavity of the upper element 6 of the slider wherein it can rotate freely, but fixed in the axial position.

In the sliding thereof, relatively to the back support, the lower element 7 of the telescopic slider is guided by lugs 9 which are fixed in the body 5 of the back support and which are moved in two cooperating through holes arranged vertically in the material of the element 7. The relative movement occurs within the limits of these holes, such that the compression spring can never expel the slider outside the body of the back support. The slider 3 as a whole remains effectively maintained in the longitudinal axis of the back support.

The bearing surface of the lower end of the compression spring 4 is shown in 42. This bottom abutment of the spring meshes as a nut with the thread of a threaded rod 44, forming a worm screw, around which the spires of the compression spring 4 are freely wound. The threaded rod 44 is mounted free in rotation but fixed in the longitudinal position through the body 5 of the back support, and outside of this, it has a knurled head 40 that makes it possible to control the rotation thereof from the outside of the back support as described above. Likewise, the abutment 42 cannot be driven in rotation with the threaded rod 44, as it is maintained immobile in rotation by the lug 41 thereof, which is guided confined in a slot 20 (FIG. 4) arranged through the wall of the body 5 of the back support. In this manner, by maneuvering the knurled head 40, the longitudinal position of the bottom abutment of the spring 4 in the body 5 of the back support is adjusted.

The harness portion of the unit according to the invention will now be described after having been disclosed in FIGS. 3 and 4 that in the lower end thereof, the body 5 of the back support forms a fastening eye 19 of strap in addition to the two lateral eyes formed by the same slots 21 and 22 as in the embodiment of FIG. 1.

FIGS. 5 and 6 show a particularly advantageous embodiment of the harness portion which is associated with the mechanical portion in the headrest device according to the invention. The assembly is shown as worn by the user thereof, the harness then maintaining the back support 2 at the top and at the centre of the back of the user. The harness is attached symmetrically and reciprocally, on each side of the back support. It comprises a top portion to which is attached the back support 2, supplemented here by a bottom portion that participates with the upper portion to maintain the back support 2 in the operational position thereof well.

The top portion of the harness comprises two shoulder straps 50 and 51 that are each attached to the respective ends of a transversal lumbar cushion 52. These shoulder straps pass through holes or slots 21, 22 of the wings of the back support and around the shoulders of the user. They are tightened at this level by tightening buckles 65, by thus stabilising the effective length of the shoulder straps, which can be adjusted by the user by pulling in front of them on the free strands of the straps. In the back of the user, the lumbar cushion 52 is directly linked to the back support 2 on which the headrest 1 is mounted, by a vertebral cushion 67, stretched by a strap that is attached in the lower eye 19 of the back support 2.

The lumbar cushion 52 is connected to the bottom portion of the harness, symmetrically by two lateral straps (the right lateral strap 57 can be seen in FIG. 6). The bottom portion is formed of two buckles 55 and 56 that tighten around the thighs on the groin section. To these two thigh buckles 55 and 56 are also respectively attached two straps 53 and 54, symmetrically on each side of the pelvis, which cross on the front of the wearer (FIG. 5) and are attached reciprocally respectively on the shoulder straps 50 and 51, not at the height of the chest, but really at the shoulders level, and more specifically in front of the collarbones. Each one of the crossed straps 53-54 is provided with a snap-fitting connector between the upper strand and the lower strand and passes through a tightening buckle, such that the user can adjust the length thereof by pulling on the free strand in front of them.

By the fact, in particular, that they intersect on the chest of the user, the straps 53 and 54 have the effect of taking away strains exerted in the back of the user by limiting as such the camber of the lumbar vertebrae and therefore by preventing traumas that can result therefrom. They act by return at the level of the shoulders, which has the effect of returning the force to the front of the pelvis. The thigh buckles 55, 56 which pass around the legs, make it possible to prevent the lumbar cushion 52 from rising up. This makes it possible to not have to tighten the top portion of the harness such that the back support remains in the position thereof. The breathing of the user is thus facilitated.

A pectoral strap 59 advantageously supplements the top portion of the harness. It is transversally arranged on the chest of the user and it is attached on each side to each one of the two shoulder straps 50 and 51 respectively. It is also of adjustable length and made from two strands that are connected together via snap-fitting. It is used mainly to connect the two shoulder straps together by pulling one towards the other on the front such that they do not risk disturbing the user via heavy friction on the ribs and under the armpits such as often result from the movements of the arms.

As for the bottom portion, it can comprise elastic strips 69 that mould the contour of the buttocks by joining in the back of the user, the thigh straps 55 and 56 respectively to the lumbar cushion 52. They prevent the thigh straps from descending on the thighs of the user when they bend forward.

The description above clearly explains how the invention makes it possible to achieve the aims that it has set. It provides a headrest device that offers great comfort for a long period of wearing time without inducing musculoskeletal strain, in particular by transmission of stresses that relieves lumbar vertebrae as well as cervical vertebrae and by a fine adaptation to the morphology of the wearer (adjustments to be made in particular by a third party on the user) and to the specific conditions in each situation of use (adjustments accessible to the user, optionally through the action of one single hand).

The invention claimed is:

1. A headrest device comprising:
 a back support comprising a telescopic slider which comprises an upper element and a lower element, wherein the upper element is axially in sliding connection with the lower element and the lower element is slidably mounted in axial translation along a longitudinal body of said back support;
 a harness configured for maintaining said back support on the back of a user wearing said device, with said longitudinal body of the back support being along the user's vertebral column when the headrest device is worn;
 a headrest configured for receiving said user's head with the occipital bone resting against the headrest when the headrest device is worn, said headrest being mounted in transverse hinged connection with an end-piece of said upper element of the slider to tilt rearwards following movements of said user's head in extension when the headrest device is worn;
 first and second elastic return means to elastically return said headrest to a nominal resting position wherein the head of the user is received on the headrest when the user is standing naturally at rest while wearing the headrest device;
 wherein said first elastic return means are adapted to return the headrest to said nominal resting position by urging the headrest against its being tilted rearwards;
 wherein said second elastic return means comprise a compression spring which is maintained guided in an axial bore arranged through the longitudinal body of the back support and through the lower element of the slider; and
 wherein an upper end of the compression spring bears on a top abutment arranged in the lower element of the slider and a bottom end of the compression spring bears on a bottom abutment formed in said longitudinal body of the back support;
 said compression spring being adapted to urge the headrest up back to the nominal position against its tending to sink into the back support body by axial translation of the slider in the longitudinal body of the back support when the headrest device is worn and the user's head moves in extension.

2. The headrest device according to claim 1, wherein the headrest is mounted mobile in tilting rearwards on the back support by rotation about a hinge rod on said end-piece of said upper element of said slider and said first elastic return means comprise a torsion spring arranged about said hinge rod and bearing on the headrest and on said end-piece of the slider.

3. The headrest device according to claim 1, further comprising means for adjusting the longitudinal position of said hinged connection between the headrest and said upper element of said slider with respect to the longitudinal body of the back support in correspondence with a neck height of the user so that the headrest supports the user's head at the level of the occipital bone when moving in extension.

4. The headrest device according to claim 1, further comprising means to adjust the stiffness of the compression spring by varying a distance between said bottom abutment and said top abutment.

5. The headset device according to claim 1, further comprising means for adjusting the force of the torsion spring by a knurled head screw being screwed through said end-piece until engagement with an abutment fixedly formed on the rear face of the headrest.

6. The headrest device according to claim 1, further comprising means for adjusting an initial stiffness of the compression spring by adjusting the position of said bottom abutment for the compression spring in the body of the back support, by a threaded rod with which said bottom abutment meshes as a nut while the nut is maintained immobile in rotation.

7. The headrest device according to claim 6, wherein said threaded rod has a knurled head accessible outside the back support.

8. The headrest device according to claim 1, further comprising an axial screw having a knurled head freely rotating in a fixed axial position in a cavity of the slider upper element and screwed into the slider lower element for adjusting an initial position of said top abutment whereon the compression spring bears at an upper end of the compression spring to adjust the nominal position of the headrest in correspondence with a neck height of the user so that the headrest supports the user's head at the level of the occipital bone when the headrest device is worn and the user's head moves in extension.

9. The headrest device according to claim 8, wherein said cavity is open and the knurled head of said axial screw is accessible through a window of said slider outside the backrest support body and thereby configured for being handled by the user when the headrest device is worn.

10. The headrest device according to claim 1, wherein the back support comprises two symmetrical wings of the longitudinal body ended with slots for attaching shoulder straps of the harness and a lower eye of said body for attaching to the body a strap stretched from a lumbar cushion of the harness.

11. The headrest device according to claim 1, wherein the headrest is mounted mobile in tilting rearwards with respect to the back support body by rotation about a transverse hinge rod affixed on said end-piece of the slider upper element and said first elastic return means comprise a torsion spring which is wound around said hinge rod and bears on a rear face of the headrest and on said end piece of the slider upper element, with a direction of winding to urge the headrest back to said nominal position when the headrest device is worn and the headrest is tilted rearwards.

12. A headrest device comprising:
a back support comprising a slider slidably mounted in axial translation along a longitudinal body of said back support;
a harness configured for maintaining said back support on the back of a user wearing said device, with said longitudinal body of the back support being along the user's vertebral column when the headrest device is worn;
a headrest configured for receiving said user's head with the occipital bone resting against the headrest when the headrest device is worn, said headrest being mounted mobile from front to rear by rotation around a transversal hinge rod connecting the headrest with an end-piece of said slider, to tilt rearwards on the back support following movements of said user's head in extension when the headrest device is worn; and
first and second elastic return means to elastically return said headrest to a nominal resting position wherein the head of said user wearing the device is received on the headrest when the headrest device is worn and said user is standing naturally at rest;
wherein said first elastic return means comprise a torsion spring arranged about said hinge rod and bearing on the headrest and on said end-piece of the slider to urge the headrest back to the nominal resting position against the headrest being tilted rearwards by rotating around the hinge rod; and
said second elastic return means comprise a compression spring bearing on a bottom abutment in said longitudinal body of the back support and on a top abutment in said slider, to urge the headrest upward against the headrest tending to sink in the back support body by axial translation of the slider along the back support body;
the headrest device being configured so that the headrest provides a non-sliding support for the user's head when the headrest device is worn and the user's head moves in extension.

13. The headrest device according to claim 12, wherein said harness comprises a top portion comprising a pair of shoulder straps attached respectively on two sides of the back support body which are capable of engaging the shoulders of a user wearing the device, and a bottom portion capable of engaging the thighs of said user;
the top portion and the bottom portion being connected by a transversal lumbar cushion in the back of said user and, on the front of said user, by two chest straps each being fixed on the bottom portion of the harness by crossing before being attached to the shoulder straps of said top portion at the level of the user's shoulders.

14. The headrest device according to claim 13, wherein said lumbar cushion is connected at the top portion of the harness to a vertebral cushion that is attached to said back support, and in the bottom portion of the harness, to two thigh straps symmetrically by two lateral straps.

15. The headrest device according to claim 13, wherein said harness comprises in the top portion of the harness, a pectoral strap transversally arranged on the chest of the user and attached on each side to each one of the shoulder straps.

16. The headrest device according to claim 13, wherein said lumbar cushion is linked to the back support by a vertebral cushion that is stretched from the lumbar cushion by a strap attached to a lower eye of the longitudinal body of the back support.

17. The headrest device according to claim 12, further comprising means for adjusting the longitudinal position of said hinge rod with respect to the longitudinal body of the back support in correspondence with a neck height of the user so that when the headrest device is worn the headrest supports the user's head at the level of the occipital bone.

18. The headrest device according to claim 12, comprising means for adjusting an initial axial position of said top abutment for the compression spring in the slider.

19. The headrest device according to claim 18, further comprising means for adjusting an initial axial position of said bottom abutment for the compression spring in the body of the back support.

20. The headrest device according to claim 12, further comprising an axial screw having a knurled head accessible through the back support and screwed into the slider for adjusting an initial position of said top abutment for the compression to adjust the nominal position of the headrest in correspondence with a neck height of the user so that the headrest supports the user's head at the level of the occipital bone when the headrest device is worn and the user's head moves in extension.

21. The headrest device according to claim 20, further comprising means for adjusting an initial stiffness of the compression spring by adjusting the position of said bottom abutment for the compression spring in the body of the back support, by a threaded rod with which said bottom abutment meshes as a nut while the nut is maintained immobile in rotation.

22. The headrest device according to claim 21, wherein said threaded rod has a knurled head accessible outside the back support.

23. The headrest device according to claim 12, wherein the slider is telescopic and comprises an upper element and a lower element, the upper element being axially in sliding connection with the lower element and the lower element being slidably mounted in axial translation in the longitudinal body of the back support, and wherein said end-piece on which the headrest is mounted mobile to tilt rearwards by rotation about said transverse hinge rod is provided at the end of said upper element.

24. A headrest device according to claim 12, wherein the back support comprises two symmetrical wings of the longitudinal body ended with slots for attaching shoulder straps of the harness and a lower eye of said body for attaching thereto a strap stretched from a lumbar cushion of the harness.

25. A headrest device comprising:
- a back support comprising a slider slidably mounted in axial translation along a longitudinal body of said back support;
- a harness configured for maintaining said back support on a back of a user wearing said device, with said longitudinal body of the back support being along the user's vertebral column when the headrest device is worn;
- a headrest configured for receiving said user's head with the occipital bone resting against the headrest when the headrest device is worn, said headrest being mounted in transversal hinged connection with an end-piece of said slider to tilt rearwards on the back support following movements of said user's head in extension when the headrest device is worn;
- first and second elastic return means to elastically return said headrest to a nominal resting position wherein said user's head is received in the headrest when the headrest device is worn while said user is standing naturally at rest, said first and second elastic return means being adapted to return the headrest to said nominal resting position by urging the headrest simultaneously against the headrest being tilted rearward and against the headrest tending to sink into the back support body by axial translation of said slider in the longitudinal body of the back support; and
- means for adjusting the longitudinal position of said hinged connection between the headrest and said slider with respect to the longitudinal body of the back support in correspondence with a neck height of the user so that when the headrest device is worn the headrest support the user's head at the level of the occipital bone when moving in extension;
- wherein the headrest is mounted mobile in tilting rearwards on the back support by rotation about a hinge rod on said end-piece of said slider and said first elastic return means comprise a torsion spring arranged about said hinge rod and bearing on the headrest and on said end-piece of the slider, said torsion spring being adapted to return the headrest elastically to said nominal resting position by urging the headrest back when tilting rearwards around said hinge rod; and
- wherein said second elastic return means comprise a compression spring bearing on a bottom abutment in said longitudinal body and on a top abutment in said slider having said end-piece, said compression spring being configured for elastically extending the slider up the back support to urge the headrest up back to the nominal resting position against the headrest tending to sink into the back support body by axial translation of said slider in the longitudinal body of the back support.

26. The headrest device according to claim 25, further comprising means to adjust the stiffness of the compression spring by varying a distance between said bottom abutment and said top abutment.

27. The headrest device according to claim 25, wherein said torsion spring is wound around said hinge rod and bears on a rear face of the headrest and on said end-piece of the slider, with a direction of winding to urge the headrest back frontwards when the headrest is tilted rearwards.

28. The headset device according to claim 27, further comprising means for adjusting the force of the torsion spring by a knurled head screw being screwed through said end-piece until engagement with an abutment fixedly formed on the rear face of the headrest.

* * * * *